United States Patent
Dandala et al.

(10) Patent No.: US 10,391,178 B2
(45) Date of Patent: Aug. 27, 2019

(54) PREMIX OF CRYSTALLINE RALTEGRAVIR POTASSIUM SALT AND A PROCESS FOR THE PREPARATION THEREOF

(71) Applicant: MYLAN LABORATORIES LTD., Maharashtra (IN)

(72) Inventors: Ramesh Dandala, Maharashtra (IN); Sivarama Prasad Vellanki, Maharashtra (IN); Raja Babu Balusu, Maharashtra (IN); Subbarayudu Putta, Maharashtra (IN)

(73) Assignee: Mylan Laboratories Limited, Hyderabad (IN)

( * ) Notice: Subject to any disclaimer, the term of this patent is extended or adjusted under 35 U.S.C. 154(b) by 167 days.

(21) Appl. No.: 15/127,612

(22) PCT Filed: Mar. 20, 2015

(86) PCT No.: PCT/IB2015/052050
§ 371 (c)(1),
(2) Date: Sep. 20, 2016

(87) PCT Pub. No.: WO2015/140765
PCT Pub. Date: Sep. 24, 2015

(65) Prior Publication Data
US 2018/0169245 A1    Jun. 21, 2018

(30) Foreign Application Priority Data

Mar. 21, 2014  (IN) .......................... 944/MUM/2014

(51) Int. Cl.
| C07D 413/12 | (2006.01) |
| A61K 31/513 | (2006.01) |
| A61K 47/26 | (2006.01) |
| A61K 9/00 | (2006.01) |
| A61K 47/38 | (2006.01) |
| A61P 31/18 | (2006.01) |

(52) U.S. Cl.
CPC ............ *A61K 47/26* (2013.01); *A61K 9/00* (2013.01); *A61K 31/513* (2013.01); *A61K 47/38* (2013.01); *C07D 413/12* (2013.01); *A61P 31/18* (2018.01); *C07B 2200/13* (2013.01)

(58) Field of Classification Search
CPC ............................ A61K 31/513; C07D 413/12
See application file for complete search history.

(56) References Cited

U.S. PATENT DOCUMENTS

| 7,754,731 | B2 | 7/2010 | Belyk | |
| 2001/0047034 | A1* | 11/2001 | Wang | ..................... A61K 47/02 |
| | | | | 514/502 |
| 2006/0122205 | A1* | 6/2006 | Belyk | ................ C07D 239/557 |
| | | | | 514/269 |

FOREIGN PATENT DOCUMENTS

| EP | 2818470 A1 | 8/2014 | |
| EP | 2818470 A1 * | 12/2014 | ........... C07D 413/12 |
| WO | WO-2011024192 A2 * | 3/2011 | ........... C07D 413/12 |
| WO | 2012103105 A1 | 8/2012 | |
| WO | 2013111100 A1 | 8/2013 | |
| WO | 2015114608 A1 | 8/2015 | |

OTHER PUBLICATIONS

International Search Report and Written Opinion of the International Searching Authority dated Jun. 9, 2015 of International Application No. PCT/IB2015/052050 filed Mar. 20, 2015.

Humphrey, Guy R., et al. "Development of a Second Generation, Highly Efficient Manufacturing Route for the HIV Integrase Inhibitor Raltegravir Potassium," Organic Process Research and Development, American Chemical Socity, U.S., vol. 15, No. 1, Jan. 21, 2011, pp. 73-83.

Wuts, Peter, et al. "Protection for the Amino Group," Greene's Protective Groups in Organic Synthesis, John Wiley & Sons, Inc., Hoboken, NJ, U.S., Apr. 10, 2006, pp. 696-926.

International Search Report and Written Opinion of the International Searching Authority dated Apr. 15, 2015 of International Application No. PCT/IB2015/050808 filed on Feb. 3, 2015.

* cited by examiner

*Primary Examiner* — Susanna Moore

(57) ABSTRACT

The present disclosure provides a process for the preparation a premix of raltegravir potassium form 3 with excipients. This premix may be used in the manufacture of pharmaceutical formulations containing raltegravir.

8 Claims, No Drawings

PREMIX OF CRYSTALLINE RALTEGRAVIR POTASSIUM SALT AND A PROCESS FOR THE PREPARATION THEREOF

CROSS-REFERENCE TO RELATED APPLICATIONS

This application, in its entirety, claims the benefit of earlier Indian provisional patent application No. 944/MUM/2014 filed on Mar. 21, 2014.

BACKGROUND OF THE INVENTION

Field of the Invention

The present invention relates generally to components of pharmaceutical formulations, and specifically, to a premix of crystalline form of raltegravir potassium salt and methods for preparing the same.

Background of the Invention

Raltegravir is an antiretroviral drug, which in its potassium salt form, is marketed under the brand name ISENTRESS® by Merck & Co. It is often used in combination with other antiretroviral drugs to treat human immunodeficiency virus (HIV) infection. Raltegravir is a first line HIV-integrase strand transfer inhibitor drug that targets integrase, an HIV enzyme that integrates viral genetic material into human chromosomes. Raltegravir potassium is chemically known as 4-[N-(4-fluorobenzyl) carbamoyl}-1-methyl-2-{1-methyl-1-(5-methyl-1,3,4-oxadiazol-2-ylcarboxamido)ethyl}-6-oxo-1,6-dihydropyrimidin-5-olate potassium salt. It has a structure represented below by Formula I.

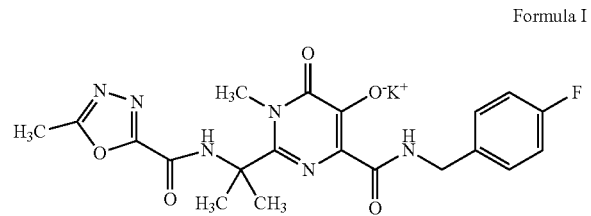

Formula I

Raltegravir and its pharmaceutically acceptable salts are disclosed in U.S. Pat. No. 7,169,780, which is hereby incorporated by reference. U.S. Pat. No. 7,754,731, which is hereby incorporated by reference, discloses crystalline Form 1, Form 2, Form 3, and amorphous forms of raltegravir potassium salt. PCT Application No. US2011/030892 (WO2011/123754), hereby incorporated by reference, discloses crystalline Forms IV, V, VI, VII, VIII IXa, IXb, X, XI, XII, XIII, XIV, XV, and XVI of raltegravir potassium salt.

The present disclosure provides a stable premix of crystalline raltegravir potassium salt which may improve certain aspects of the manufacturing of pharmaceutical formulations that contain raltegravir.

SUMMARY OF THE INVENTION

One aspect of the present disclosure is to provide a premix of crystalline raltegravir potassium salt and a process for the preparation thereof.

One embodiment of the present invention provides a process for the preparation of the premix of crystalline form of raltegravir potassium salt which may include the following steps:
1. dissolving raltegravir in a suitable solvent,
2. adding a source of potassium to the raltegravir solution,
3. adding pharmaceutical excipients or mixtures thereof to form a reaction mass,
4. cooling the reaction mass, and
5. isolating crystalline raltegravir potassium premix.

DETAILED DESCRIPTION OF THE INVENTION

The present disclosure provides a crystalline premix of raltegravir potassium salt and a process for the preparation thereof.

Within the context of the present invention, the premix of raltegravir potassium is prepared from raltegravir potassium and pharmaceutically acceptable excipients.

One aspect of the present invention provides a method for the preparation of the premix of crystalline form of raltegravir potassium salt which may be performed by the following steps:
1. dissolving raltegravir in a suitable solvent,
2. adding a potassium source to the raltegravir solution,
3. adding a pharmaceutical excipient or mixtures thereof to form a reaction mass,
4. cooling the reaction mass, and
5. isolating crystalline raltegravir potassium premix.

Another aspect of the present invention discloses a premix of crystalline raltegravir potassium form 3, which may be prepared by the following steps:
1. dissolving raltegravir in an ester solvent,
2. adding a potassium source to the raltegravir solution,
3. adding a pharmaceutical excipient or mixtures thereof to form a reaction mass,
4. cooling the reaction mass, and
5. isolating the premix of crystalline raltegravir potassium form 3.

According to the present invention, raltegravir is dissolved in an ester solvent to create a raltegravir solution. Any form of raltegravir may be used as a starting material. In some embodiments, the raltegravir free base was found to be a particularly useful a starting material. The ester solvent may be, for example, ethyl acetate, n-butyl acetate, n-propyl acetate, t-butyl acetate, isopropyl acetate, or mixtures thereof. In some embodiments, it has been found that ethyl acetate is a particularly useful ester solvent to use for this step.

Next, a potassium source is added to the raltegravir solution. The source of potassium may be, for example, an alcoholic potassium hydroxide or aqueous potassium hydroxide. In some embodiments, alcoholic potassium hydroxide was found to be particularly useful. Examples of suitable alcoholic potassium hydroxides include methanolic potassium hydroxide and ethanolic potassium hydroxide. Methanolic potassium hydroxide, in some embodiments, was found to particularly useful. Within the context of the present invention, the methanolic potassium hydroxide may be prepared by dissolving potassium hydroxide pellets in methanol at a concentration of about 3% potassium hydroxide to about 15% potassium hydroxide. Other potassium hydroxide sources may be prepared in a similar way by dissolving potassium hydroxide pellets in an alcoholic solvent or water.

According to the present disclosure, a pharmaceutical excipient or mixtures thereof are then added to the raltegravir potassium solution. Within the context of the present invention, pharmaceutical excipient may include diluents, lubricants, disintegrants, glidants, stabilizers, surface active agents, anti-adherents, opacifiers, solvents, colorants, lubricants, pigments, anti-foam agents, and polishing agents. In some embodiments, microcrystalline cellulose, polysorbate, mannitol, and hydroxypropyl methylcellulose were found to be particularly useful excipients. Within the context of the present invention, the excipient or combinations of excipients may be included in the formulation at a weight ratio of 0.01:1 to 20:1 (w/w) with respect to raltegravir potassium.

Examples of useful pharmaceutical excipients within the context of the present invention include starches, lactose, mannitol (for example, PEARLITOL™ SD200), cellulose and cellulose derivatives, and confectioner's sugar. Different forms of lactose may be useful in the context of the present invention, for example, lactose monohydrate, lactose DT (direct tableting), and lactose anhydrous. Different forms of starches may be used in the context of the present invention, for example, maize starch, potato starch, rice starch, wheat starch, pre-gelatinized starch, starch 1500, starch 1500 LM grade, fully pre-gelatinized starch. Examples of suitable cellulose compounds for use in the context of the present invention include crystalline celluloses, such as CEOLUS™ KG-801, and a variety of AVICEL™ celluloses (for example, PH-101, PH-102, PH-301, PH-302, PH-F20, PHI-12, PH-114, and PH-112). Powdered celluloses may be used as well. Other useful cellulose derivatives include hydroxypropylcelluloses (HPCs, examples include KLUCEL™ LF and KLUCEL™ EXF), low-substituted hydroxypropylellulcoses (L-HPCS, examples include LH-11, LH-21, LH-31, LH-22, LH-32, LH-20, LH-30, LH-32 and LH-33), hydroxypropylmethylcelluloses (also called hypromelloses or HPMC, one example is METHOCEL™). Other suitable binders/disintegrants include polyvinylpyrrolidones (also called povidones; examples include PVP-K25, PVP-K29, PVP-K30, and PVP-K90), copovidone (for example, PLASDONE™ S-630). Other suitable excipients include powdered acacia, gelatin, guar gum, sodium starch glycolate, colloidal silicon dioxide, carbomers (for example, CARBOPOL™), methylcelluloses, polymethacrylates, carmellose calcium, carboxymethyl starch sodium, croscarmellose sodium, and crospovidones (for example, cross-linked povidone, KOLLIDON™ CL, POLYPLASDONE™ XL, XI-I 0, and INF-10). Further examples of suitable excipients include sorbitan esters (for example, SPAN™), polyhydroxyethylenically-treated sorbitan esters (for example, TWEEN™), aliphatic alcohols and PEG ethers, phenol and PEG ethers, quaternary ammonium salts (e.g., cetyltrimethylammonium bromide), amine salts (for example, octadecylamine hydrochloride), stearates (for example, glyceryl monostearates, polyoxyethylene monostearates, ethylene glycol stearates, propylene glycol stearates, diethylene glycol stearates, glycerol stearates, sodium stearate, potassium stearate, ammonium stearate, calcium stearate, sodium stearate, triethenolamine stearate, zinc stearate, and magnesium stearate), sodium lauryl sulfate, magnesium lauryl sulfate, calcium and sodium soaps, sodium dioctylsulfosuccinate, sodium dodecylbenzenesulfonate, palmitic acid, talc, carnauba wax, silicate, silicon dioxide, hydrogenated vegetable oils and fats, stearic acid, and combinations thereof. Phospholipids (e.g., diacylphosphatidylglycerols, diaceylphosphatidylcholines, and diaceylphosphatidic acids, the precursors and derivatives thereof, such as soybean lecithin and egg yolk) may also be used. Examples of suitable pigments include titanium oxide, silicon dioxide, iron oxides, zinc oxide, and combinations thereof. Suitable plasticizers include, as examples, castor oil, diacetylated monoglycerides, dibutyl sebacate, diethyl phthalate, glycerin, polyethylene glycol, propylene glycol, triacetin, and triethyl citrate. Suitable basic inorganic salts of sodium, potassium, magnesium, and calcium (e.g., sodium carbonate, sodium hydrogen carbonate, sodium hydroxide, potassium carbonate, calcium carbonate, magnesium carbonate, dibasic calcium phosphate, tribasic calcium phosphate, potassium hydrogen carbonate, potassium hydroxide, heavy magnesium carbonate, magnesium, $[Mg_6Al(OH)_{16}.CO_3.4H_2O]$, aluminum hydroxide-magnesium, and $[2.5MgO.Al_2O_3.H_2O]$ may be include in the formulation as well.

Many of the excipients listed above can act in a multitude of functional roles (e.g., starches can act both as a disintegrants and a binder depending on the formulation) to dictate the final properties of the desired product. One of skill in the art will readily recognize these various functional aspects of each excipient and be able to incorporate, without undue experimentation, an excipient or combinations of excipients to achieve the desired final product.

In some embodiments, microcrystalline cellulose, mannitol, and mixtures thereof have been found to particularly useful excipients for creating a premix of crystalline raltegravir potassium form 3.

In some embodiments of the present invention, the excipient or mixture of excipients included in the premix of crystalline raltegravir potassium form 3 may be insoluble in an organic solvent.

After adding excipients to the raltegravir potassium reaction mass, the reaction mass is then cooled. Within the context of the present invention, the reaction mass may be cooled to a temperature of approximately −5 to 10° C. In some embodiments, a temperature between about 0-10° C. was found to be particularly useful. In other embodiments, a temperature of about 0-5° C. was found to be particularly useful. The resulting product may then be filtered to isolate the premix of crystalline raltegravir potassium form 3. The product may then be washed with an appropriate solvent, for example, with ethyl acetate. The product then may be dried to result in the final product of the premix of crystalline raltegravir potassium form 3.

Premixes of raltegravir potassium salts, prepared by the processes disclosed in the present invention, may be incorporated into a pharmaceutical formulation useful for the treatment of HIV in human patients. Numerous types of pharmaceutical formulations may be employed, including tablets, chewable tablets, and oral suspensions. In addition to the excipients disclosed above to create a premix, other excipients may be added prior to final formulation of the final dosage form for example, one or more of diluents, binders, stabilizers, lubricants, glidants, disintegrating agents, surfactants, and other additives that are commonly used in solid pharmaceutical dosage form preparations. When formulated as a tablet, the product may be prepared by various methods known in the art such as by dry granulation, wet granulation, melt granulation, direct compression, extrusion spheronization and the like. The formulation may include such excipients as calcium phosphate dibasic anhydrous, hypromellose, lactose monohydrate, magnesium stearate, microcrystalline cellulose, croscarmellose sodium, poloxamer 407 (contains 0.01% butylated hydroxytoluene as antioxidant), sodium stearyl fumarate. In addition, the tablet may include a film coating that may contain the following inactive ingredients: black iron oxide, polyethylene glycol 3350, polyvinyl alcohol, red iron oxide, talc and titanium dioxide. In some embodiments, the raltegravir or pharmaceutically acceptable salts thereof may be included in a chewable tablet. Such formulations may include, as examples of appropriate excipients, ammonium hydroxide, crospovidone, ethylcellulose 20 cP, fructose, hydroxypropyl cellulose, hypromellose 2910/6 cP, magnesium stearate, mannitol, medium chain triglycerides, monoammonium glycyrrhizinate, natural and artificial flavors (orange, banana, and masking that contains aspartame), oleic acid, PEG 400, red iron oxide, saccharin sodium, sodium citrate dihydrate, sodium stearyl fumarate, sorbitol, sucralose and yellow iron oxide. In other embodiments, the pharmaceutical formulation may be an oral suspension. The formulation intended for oral suspension may include excipients such as ammonium hydroxide, artificial flavorings, natural flavorings, carboxymethylcellulose sodium, crospovidone, ethylcellulose 20 cP, fructose, hydroxypropyl cellulose, hypromellose 2910/6 cP, macrogol/PEG 400, magnesium stearate, maltodextrin, mannitol, medium chain triglycerides, microcrystalline cellulose, monoammonium glycyrrhizinate, oleic acid, sorbitol, sucralose, and sucrose.

In treatment of patients with HIV, raltegravir potassium salt premixes, prepared by the processes disclosed in the present invention, may also be administered in conjunction with other active pharmaceutical ingredients, including efavirenz, fosamprenavir, ritonavir, tipranavir, rifampin, tenofovir, lamivudine, and emtricitabine.

In view of the above description and the examples below, one of ordinary skill in the art will be able to practice the invention as claimed without undue experimentation. The foregoing will be better understood with reference to the following examples that detail certain procedures for the preparation of molecules, compositions and formulations according to the present invention. All references made to these examples are for the purposes of illustration. The following examples should not be considered exhaustive, but merely illustrative of only a few of the many aspects and embodiments contemplated by the present disclosure.

Example 1: Preparation a Premix of Crystalline Raltegravir Potassium Form 3 with Microcrystalline Cellulose and Mannitol Raltegravir (50 g) free base was dissolved in 4500 ml of ethyl acetate. Methanolic potassium hydroxide solution (6.50 g of potassium hydroxide pellets in 70 ml of methanol) was then added. Microcrystalline cellulose (45 g) and mannitol (41.1 g) were added to the raltegravir potassium reaction mass and stirred for 10 minutes. The reaction mass was cooled to 0-5° C. and maintained for 2 hours at same temperature. The resulting product was filtered, washed with ethyl acetate, and dried under vacuum for 12-15 hours at 30° C. to obtain 130 g of a premix of crystalline raltegravir potassium form 3 with microcrystalline cellulose and mannitol.

Example 2: Preparation of Premix of Crystalline Raltegravir Potassium Form 3 with Microcrystalline Cellulose Raltegravir (50 g) free base was dissolved in 4500 ml of ethyl acetate. Methanolic potassium hydroxide solution (6.50 g of potassium hydroxide pellets in 70 ml of methanol) was then added. Microcrystalline cellulose (45 g) was added to the raltegravir potassium reaction mass and stirred for 10 minutes. The reaction mass was cooled to 0-5° C. and maintained for 2 hours at same temperature. The resulting product was filtered, washed with ethyl acetate, and dried under vacuum for 12-15 hours at 30° C. to obtain 90 g of a premix of crystalline raltegravir potassium form 3 with microcrystalline cellulose.

Example 3: Preparation of Premix of Crystalline Raltegravir Potassium Form 3 with Mannitol Raltegravir (50 g) free base was dissolved in 4500 ml of ethyl acetate. Methanolic potassium hydroxide solution (6.50 g of potassium hydroxide pellets in 70 ml of methanol) was then added. Mannitol (41.1 g) was added to the raltegravir potassium reaction mass and stirred for 10 minutes. The reaction mass was cooled to 0-5° C. and maintained at same temperature for 2 hours. The resulting product was filtered, washed with ethyl acetate, and dried under vacuum for 12-15 hours at 30° C. to obtain 90 g of a premix of crystalline raltegravir potassium form 3 with mannitol.

Example 4: Preparation of Premix of Crystalline Raltegravir Potassium Form 3 with Polysorbate Raltegravir (50 g) free base was dissolved in 4500 ml of ethyl acetate. Methanolic potassium hydroxide solution (6.50 g of potassium hydroxide pellets in 70 ml of methanol) was then added. Refined polysorbate 80 (5.0 g) was added to the raltegravir potassium reaction mass and stirred for 10 minutes. The reaction mass was cooled to 0-5° C. and maintained at same temperature for 2 hours. The resulting product was filtered, washed with ethyl acetate, and dried under vacuum for 12-15 hours at 30° C. to obtain 90 g of Raltegravir Potassium form-3 premix with polysorbate.

Example 5: Preparation of Premix of Crystalline Raltegravir Potassium Form 3 with Hydroxypropyl Methylcellulose (HPMC)

Raltegravir (50 g) free base was dissolved in 4500 ml of ethyl acetate at reflux temperature. Methanolic potassium hydroxide solution (6.50 g of potassium hydroxide pellets in 70 ml of methanol) was then added at ambient temperature. Hydroxy propyl methyl cellulose (HPMC) (12.5 g) was added to the raltegravir potassium reaction mass and stirred for 10 minutes. The reaction mass was cooled to 0-5° C. and maintained at same temperature for 2 hours. The resulting solid product was filtered and washed with ethyl acetate. The resulting product was dried under vacuum for 8 hours at 30° C., and further dried at 40° C. for another 8 hours, to obtain 55 g of Raltegravir Potassium form-3 premix with HPMC.

Example 6: Preparation of Premix of Crystalline Raltegravir Potassium Form 3 with Hydroxypropyl Methylcellulose (HPMC)

Raltegravir (50 g) free base was dissolved in 2500 ml of ethyl acetate at reflux temperature. Methanolic potassium hydroxide solution (6.50 g of potassium hydroxide pellets in 70 ml of methanol) was then added at ambient temperature. HPMC (5.0 g) was added to the raltegravir potassium reaction mass and stirred for 10 minutes. The reaction mass was cooled to 0-5° C. and maintained at same temperature for 2 hours. The resulting product was filtered and washed with ethyl acetate and dried under vacuum for 8 hours at 30° C., then further dried at 40° C. for another 8 hours, to obtain 48 g of Raltegravir Potassium form-3 premix with HPMC.

We claim:

1. A process for preparing a premix of raltegravir potassium form 3, the process comprising the steps of:
    (a) dissolving raltegravir free base in an ester solvent to create a solution;
    (b) adding a potassium source to the solution;
    (c) adding a pharmaceutical excipient to form a reaction mass;
    (d) cooling the reaction mass; and
    (e) isolating the raltegravir potassium form 3 premix from the reaction mass, the raltegravir potassium form 3 premix comprising raltegravir potassium form 3 and the pharmaceutical excipient, wherein the pharmaceutical excipient is at least one of microcrystalline cellulose, polysorbate, mannitol, or hydroxypropyl methylcellulose.

2. The process according to claim 1, wherein the ester solvent is selected from the group consisting of ethyl acetate, n-butyl acetate, n-propyl acetate, t-butyl acetate, isopropyl acetate, and combination thereof.

3. The process according to claim 1, wherein the potassium source an alcoholic potassium hydroxide or aqueous potassium hydroxide.

4. The process according to claim 3, wherein the alcoholic potassium hydroxide is selected from the group consisting of methanolic potassium hydroxide or ethanolic potassium hydroxide.

5. The process according to claim 1, further comprising adding a second pharmaceutical excipient in step (c).

6. The process according to claim 5, wherein the pharmaceutical excipient and the second pharmaceutical excipient are selected from the group consisting of microcrystalline cellulose, polysorbate, mannitol, and hydroxypropyl methylcellulose.

7. The process according to claim 1, wherein the cooling step includes cooling the reaction mass to a temperature between about −5° C. and about 10° C.

8. The process according to claim 1, wherein said isolating step comprises filtering the reaction mass.

\* \* \* \* \*